(12) United States Patent
Liu

(10) Patent No.: US 11,369,758 B2
(45) Date of Patent: Jun. 28, 2022

(54) ELECTRONIC CIGARETTE HAVING PRESS BUTTON FOR ADJUSTING VAPOR AMOUNT

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 247 days.

(21) Appl. No.: 16/581,792

(22) Filed: Sep. 25, 2019

(65) Prior Publication Data

US 2020/0315264 A1 Oct. 8, 2020

(30) Foreign Application Priority Data

Apr. 4, 2019 (CN) .......................... 201910273335.3
Apr. 4, 2019 (CN) .......................... 201920461532.3

(51) Int. Cl.
*A24F 13/00* (2006.01)
*A24F 17/00* (2006.01)
*A24F 25/00* (2006.01)
*A61M 11/04* (2006.01)
*A24F 40/10* (2020.01)
*A24F 40/40* (2020.01)

(52) U.S. Cl.
CPC ........... *A61M 11/042* (2014.02); *A24F 40/10* (2020.01); *A24F 40/40* (2020.01); *A61M 2205/8206* (2013.01)

(58) Field of Classification Search
CPC ................................. A24F 40/10; A24F 40/40
See application file for complete search history.

(56) References Cited

U.S. PATENT DOCUMENTS

| 2014/0290677 | A1* | 10/2014 | Liu ........................ A61M 15/06 131/329 |
| 2016/0150824 | A1* | 6/2016 | Memari .................. A24F 40/40 131/329 |
| 2016/0366946 | A1* | 12/2016 | Murison .............. H05B 1/0244 |
| 2017/0043999 | A1* | 2/2017 | Murison .............. A61M 11/042 |
| 2017/0045150 | A1* | 2/2017 | Marsh ..................... A24F 15/18 |
| 2017/0045994 | A1* | 2/2017 | Murison ................. H02J 7/342 |
| 2017/0064997 | A1* | 3/2017 | Murison .............. B67D 7/0294 |
| 2017/0099878 | A1* | 4/2017 | Murison ............... A24F 15/015 |
| 2018/0184722 | A1* | 7/2018 | Murison ................. A24F 40/95 |
| 2019/0297953 | A1* | 10/2019 | Qiu ....................... A61M 11/042 |
| 2020/0119489 | A1* | 4/2020 | Novak, III .......... H01R 13/6205 |
| 2020/0359692 | A1* | 11/2020 | Liu .......................... A24F 40/42 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette including an atomization assembly and a battery assembly. The atomization assembly includes a first housing; a heating wire; a limit cover; a first silicone seal sealing the limit cover; a monolayer nonwoven fabric; a multilayer nonwoven fabric; a fixed seat fixing the heating wire; an insulation ring; a joint; a silicone gasket sealing the fixed seat; a sealing seat; a first seal ring; an e-liquid injection seat; a spring; a funnel; a second seal ring sealing the funnel; a second silicone seal; a cover; and a first magnet. The battery assembly includes a third silicone seal sealing a pneumatic switch; a support plate supporting the pneumatic switch; a control plate; a position limiter limiting the control plate; a battery core; a second magnet; a third seal ring; a support supporting the control plate; a decorative plate; a second housing; and a press button.

1 Claim, 5 Drawing Sheets

ELECTRONIC CIGARETTE HAVING PRESS BUTTON FOR ADJUSTING VAPOR AMOUNT

CROSS-REFERENCE TO RELATED APPLICATIONS

Pursuant to 35 U.S.C. § 119 and the Paris Convention Treaty, this application claims foreign priority to Chinese Patent Application No. 201910273335.3 filed Apr. 4, 2019, and to Chinese Patent Application No. 201920461532.3 filed Apr. 4, 2019. The contents of all of the aforementioned applications, including any intervening amendments thereto, are incorporated herein by reference.

BACKGROUND

The disclosure relates to an electronic cigarette.

Electronic cigarettes atomize nicotine-containing e-liquid.

Conventionally, the atomization assembly is fixedly attached to the battery assembly resulting in difficult replacement or repair of individual parts.

SUMMARY

The disclosure provides an electronic cigarette.

The electronic cigarette comprises an atomization assembly and a battery assembly. The atomization assembly is disposed on the battery assembly.

The atomization assembly comprises a first housing of a tank for storing liquid; a heating wire; a limit cover limiting the heating wire; a first silicone seal sealing the limit cover; a monolayer nonwoven fabric; a multilayer nonwoven fabric; a fixed seat fixing the heating wire; an insulation ring; a joint; a silicone gasket sealing the fixed seat; a sealing seat; a first seal ring; an e-liquid injection seat; a spring; a funnel; a second seal ring sealing the funnel; a second silicone seal; a cover; and a first magnet.

The battery assembly comprises a third silicone seal sealing a pneumatic switch; a support assembly supporting the pneumatic switch; a control plate; a position limiter limiting the control plate; a battery core; a second magnet; a third seal ring; a support supporting the control plate; a decorative plate; a second housing; and a press button.

The first magnet is disposed in the cover; the second silicone seal is disposed on the cover; the cover is embedded in first housing of the tank for storing liquid; the spring and the second seal ring are sequentially disposed on the funnel in that order; the spring, the second seal ring, and the funnel are disposed within the e-liquid injection seat; the first seal ring is disposed on the sealing seat, and the sealing seat is disposed on the funnel; the e-liquid injection seat is disposed in a side hole of the cover; the multilayer nonwoven fabric is sheathed on the heating wire; the heating wire is disposed in the fixed seat; the insulation ring and the joint are sequentially disposed in the fixed seat in that order; the silicone gasket is sheathed on the fixed seat; the monolayer nonwoven fabric is sheathed on the fixed seat; the fixed seat is disposed in the limit cover; the first silicone seal is disposed on the limit cover; the positive and negative terminals of the battery core are connected to the support assembly; the control plate is disposed on the support assembly; the third silicone seal is disposed on the support assembly; the support assembly is disposed in the support; the position limiter is disposed on the support; the third seal ring is sheathed on the support; the second magnet is disposed in the support; the press button is disposed on the second housing; the support is disposed in the housing; and the decorative plate is attached to the housing. The e-liquid is directly injected into the atomization assembly by pressing the funnel, and the funnel can be repeatedly used for injection of the e-liquid.

Advantages of the electronic cigarette according to embodiments of the disclosure are summarized as follows. The press button comprises two tap positions. Continuous pressing the press button can adjust the output amount of the vapor. For example, continuously press the press two times, the electronic cigarette can output a maximum amount of vapor. The output voltage periodically changes in two values as per the press times of the press button. The atomization assembly is magnetically connected to the battery assembly through the first magnet and the second magnet.

DETAILED DESCRIPTION

Figure 1:
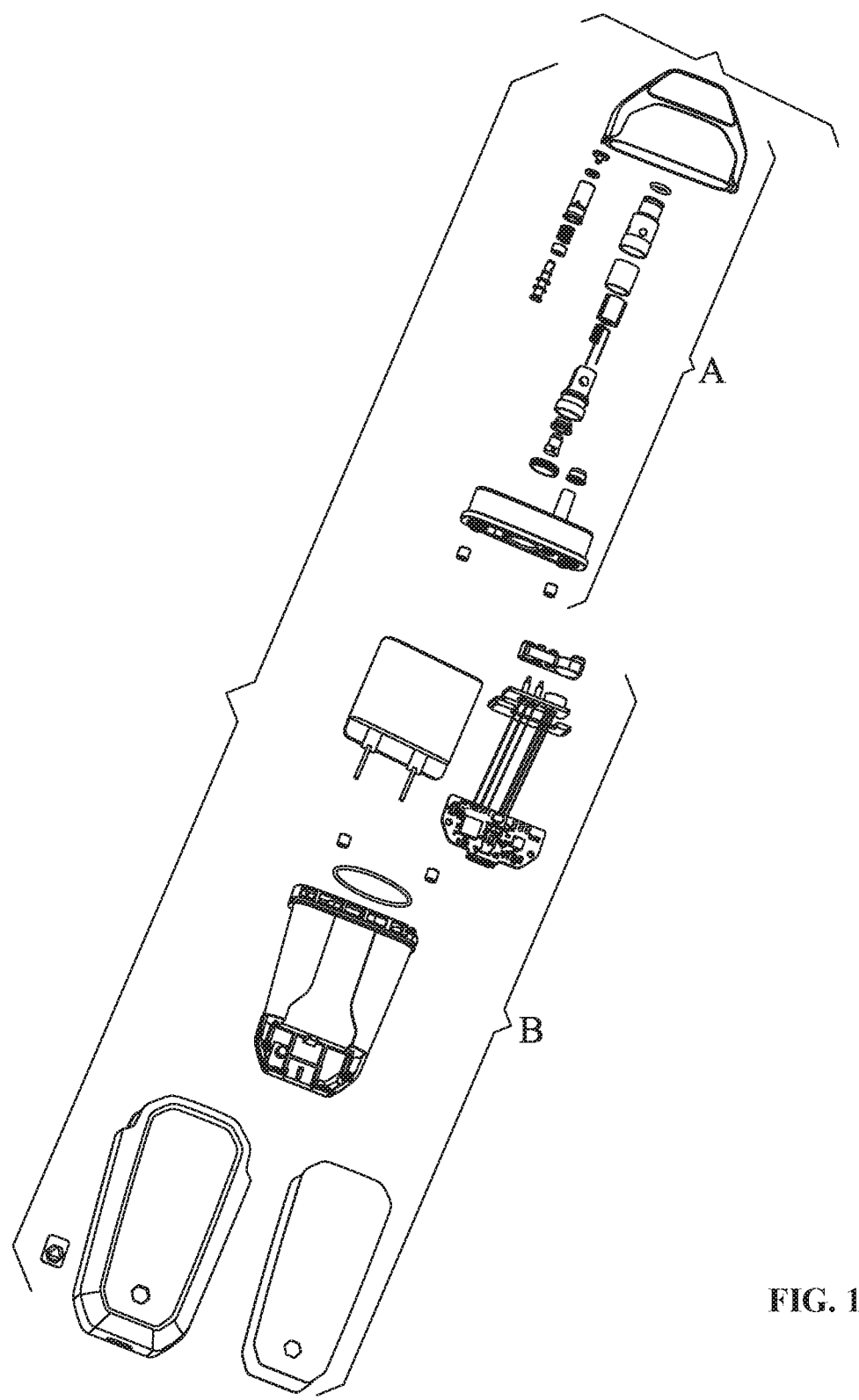
FIG. 1 is an exploded view of an electronic cigarette according to one embodiment of the disclosure.
Figure 2:
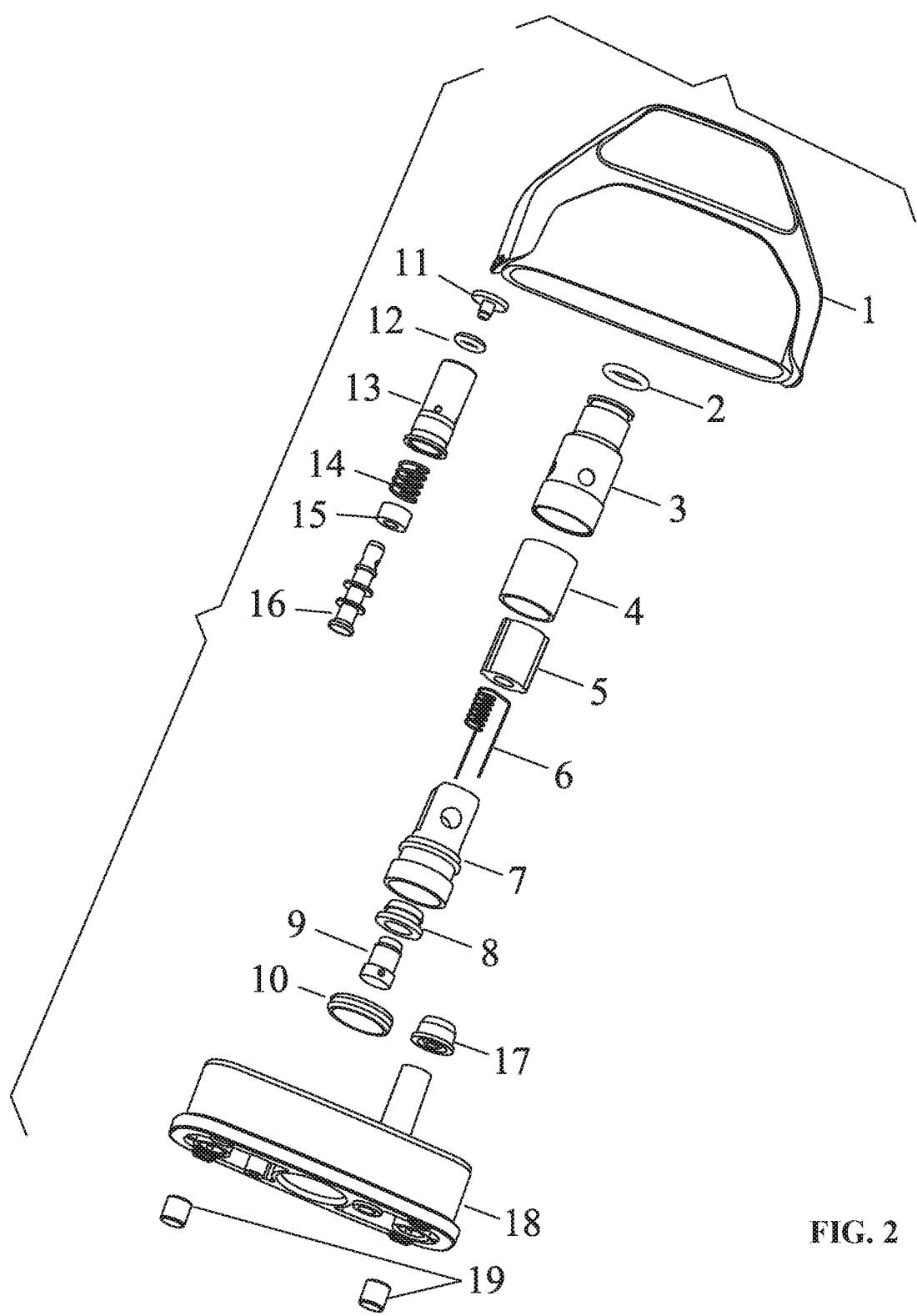
FIG. 2 is an exploded view of an atomization assembly of an electronic cigarette according to one embodiment of the disclosure.
Figure 3:
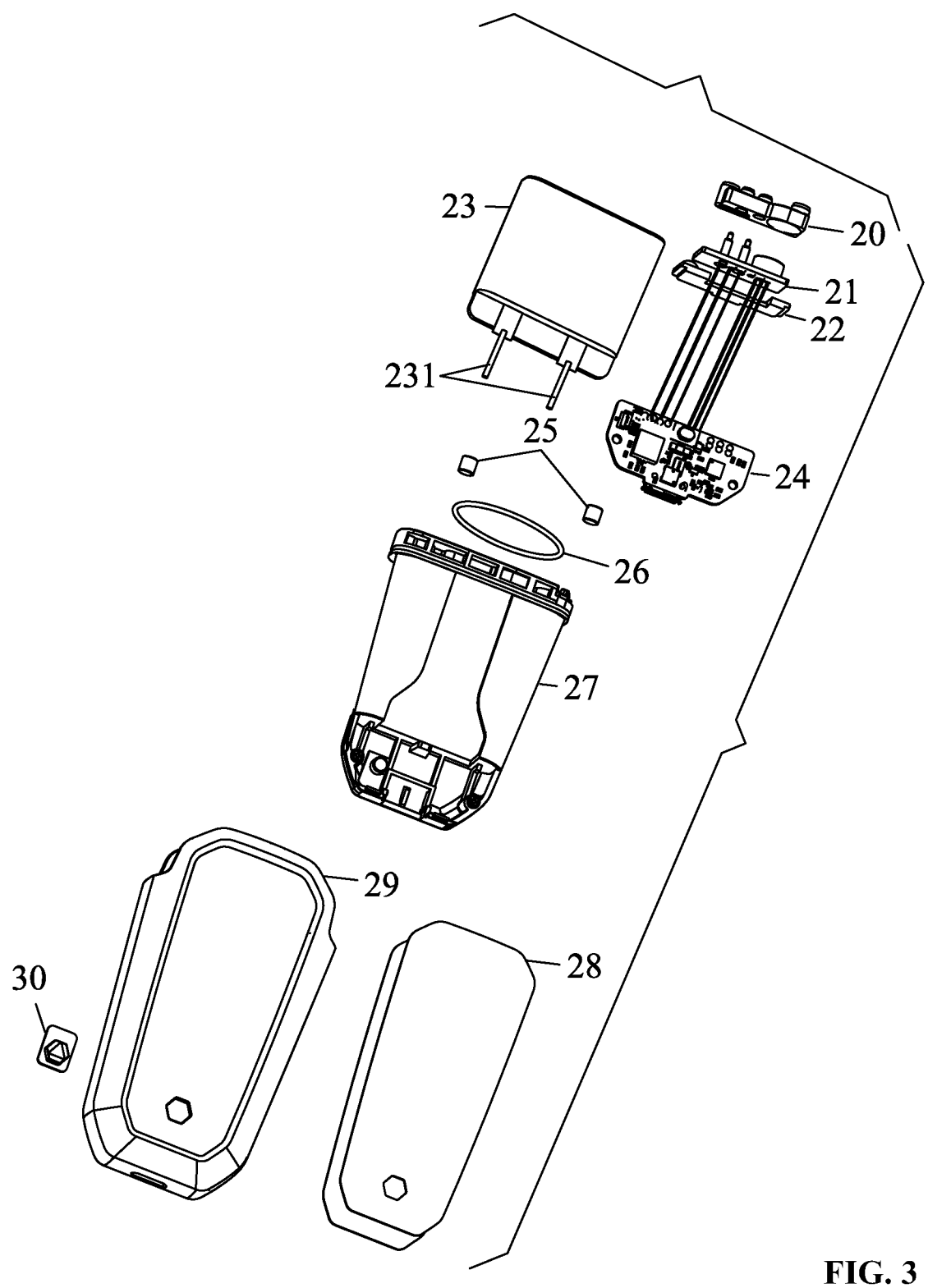
FIG. 3 is an exploded view of a battery assembly of an electronic cigarette according to one embodiment of the disclosure.
Figure 4:
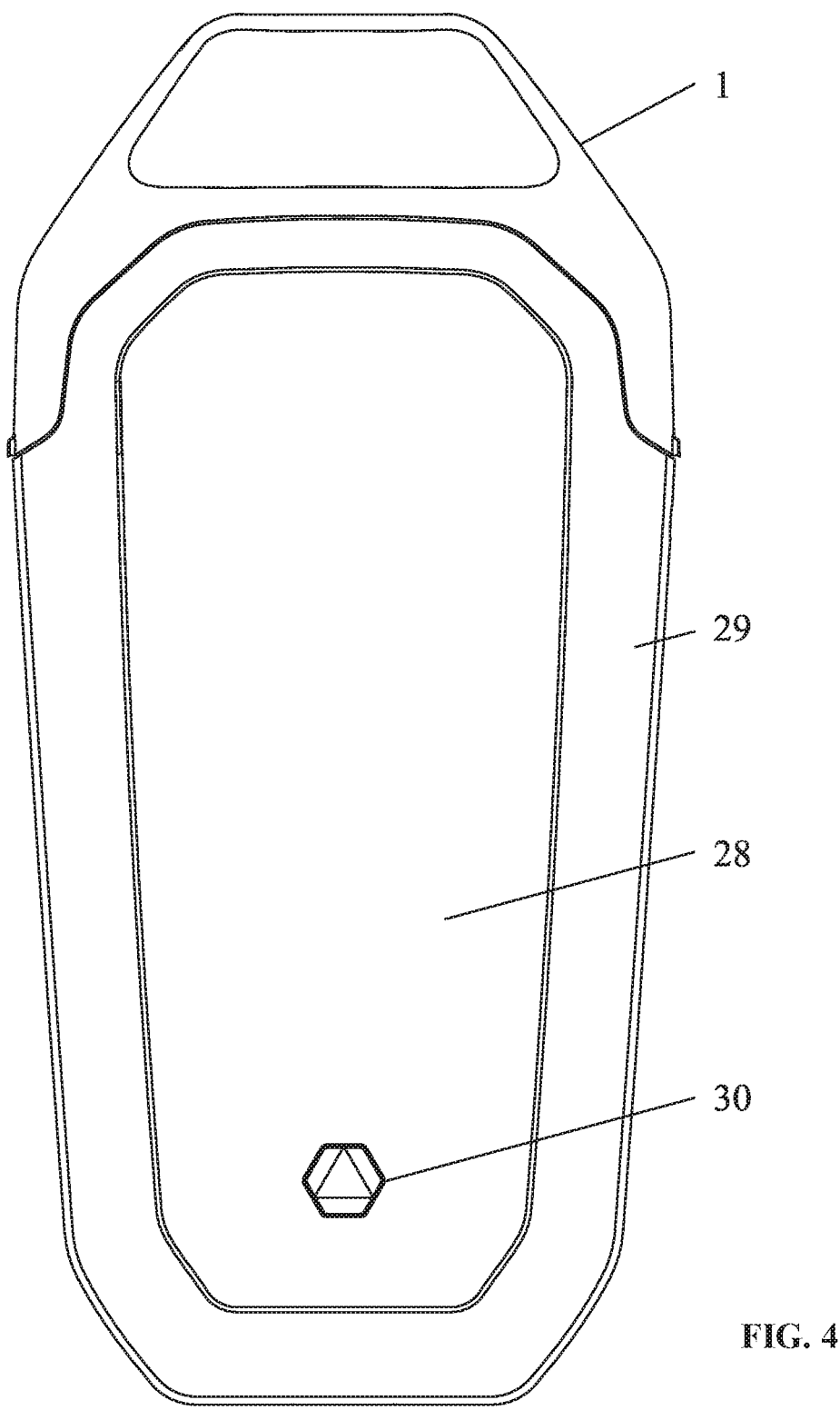
FIG. 4 is a schematic diagram of an electronic cigarette according to one embodiment of the disclosure.
Figure 5:
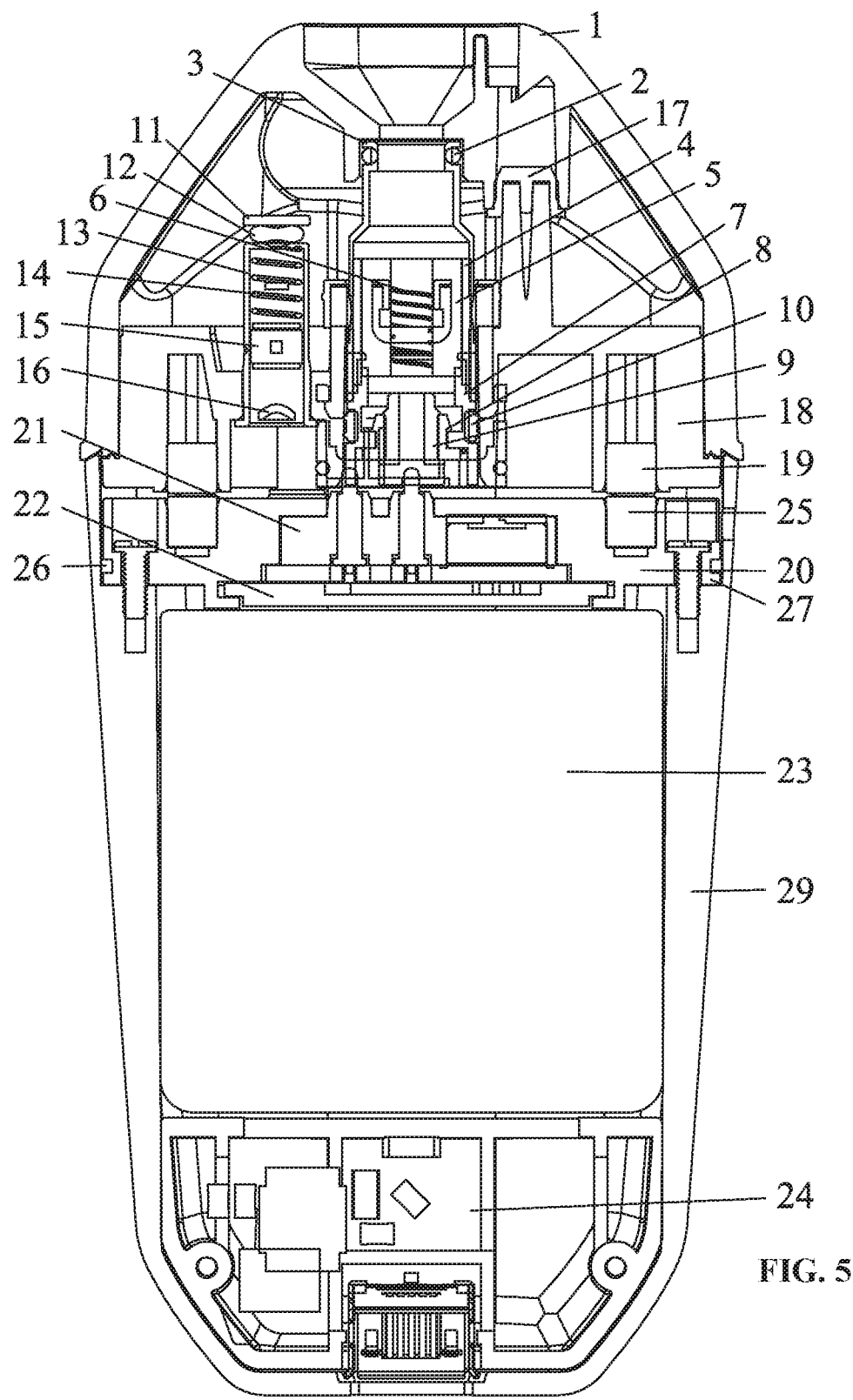
FIG. 5 is a sectional view of an electronic cigarette according to one embodiment of the disclosure.

To further illustrate, embodiments detailing an electronic cigarette are described below. It should be noted that the following embodiments are intended to describe and not to limit the disclosure.

An electronic cigarette comprises an atomization assembly A and a battery assembly B. The atomization assembly A is disposed on the battery assembly B.

The atomization assembly A comprises a first housing 1 of a tank for storing liquid; a heating wire 6; a limit cover 3 limiting the heating wire 6; a first silicone seal 2 sealing the limit cover 3; a monolayer nonwoven fabric 4; a multilayer nonwoven fabric 5; a fixed seat 7 fixing the heating wire 6; an insulation ring 8; a joint 9; a silicone gasket 10 sealing the fixed seat 7; a sealing seat 11; a first seal ring 12; an e-liquid injection seat 13; a spring 14; a funnel 16; a second seal ring 15 sealing the funnel 16; a second silicone seal 17; a cover 18; and a first magnet 19.

The battery assembly comprises a third silicone seal 20 sealing a pneumatic switch; a support assembly 21 supporting the pneumatic switch; a control plate 24; a position limiter 22 limiting the control plate 24; a battery core 23; a second magnet 25; a third seal ring 26; a support 27 supporting the control plate 24; a decorative plate 28; a second housing 29; and a press button 30.

The first magnet 19 is disposed in the cover 18; the second silicone seal 17 is disposed on the cover 18; the cover 18 is embedded in first housing 1 of the tank for storing liquid; the spring 14 and the second seal ring 15 are sequentially disposed on the funnel 16 in that order; the spring 14, the second seal ring 15, and the funnel 16 are disposed within the e-liquid injection seat 13; the first seal ring 12 is disposed on the sealing seat 11, and the sealing seat 11 is disposed on the funnel 16; the e-liquid injection seat 13 is disposed in a side hole of the cover 18; the multilayer nonwoven fabric 5 is sheathed on the heating wire 6; the heating wire 6 is disposed in the fixed seat 7; the insulation ring 8 and the joint 9 are sequentially disposed in the fixed seat 7 in that order; the silicone gasket 10 is sheathed on the fixed seat 7; the monolayer nonwoven fabric 4 is sheathed on the fixed seat 7; the fixed seat 7 is disposed in the limit cover 3; the first silicone seal 2 is disposed on the limit cover 3; the positive and negative terminals 231 of the battery core 23 are connected to the support assembly 21; the control plate 24 is disposed on the support assembly 21; the third silicone seal 20 is disposed on the support assembly 21; the support assembly 21 is disposed in the support 27; the position limiter 22 is disposed on the support 27; the third seal ring 26 is sheathed on the support 27; the second magnet 25 is disposed in the support 27; the press button 30 is disposed on the second housing 29; the support 27 is disposed in the housing 29; and the decorative plate 28 is attached to the housing 29. The e-liquid is directly injected into the atomization assembly by pressing the funnel 16, and the funnel 16 can be repeatedly used for injection of the e-liquid.

The press button 30 comprises two tap positions. Continuous pressing the press button can adjust the output amount of the vapor. For example, continuously press the press two times, the electronic cigarette can output a maximum amount of vapor. The output voltage periodically changes in two values as per the press times of the press button. The atomization assembly is magnetically connected to the battery assembly through the first magnet and the second magnet.

It will be obvious to those skilled in the art that changes and modifications may be made, and therefore, the aim in the appended claims is to cover all such changes and modifications.

What is claimed is:

1. A device, comprising:
   1) an atomization assembly, the atomization assembly comprising:
      a first housing of a tank for storing liquid;
      a heating wire;
      a limit cover limiting the heating wire;
      a first silicone seal sealing the limit cover;
      a monolayer nonwoven fabric;
      a multilayer nonwoven fabric;
      a fixed seat fixing the heating wire;
      an insulation ring;
      a joint;
      a silicone gasket sealing the fixed seat;
      a sealing seat;
      a first seal ring;
      an e-liquid injection seat;
      a spring;
      a funnel;
      a second seal ring sealing the funnel;
      a second silicone seal;
      a cover; and
      a first magnet; and
   2) a battery assembly, the battery assembly comprising:
      a third silicone seal;
      a support assembly;
      a control plate;
      a position limiter limiting the control plate;
      a battery core;
      a second magnet;
      a third seal ring;
      a support supporting the control plate;
      a decorative plate;
      a second housing; and
      a press button;

wherein:
      the first magnet is disposed in the cover; the second silicone seal is disposed on the cover; the cover is embedded in the first housing; the spring and the second seal ring are sequentially disposed on the funnel in that order; the spring, the second seal ring, and the funnel are disposed within the e-liquid injection seat; the first seal ring is disposed on the sealing seat, and the sealing seat is disposed on the funnel; the e-liquid injection seat is disposed in the cover and extends into interior of the first housing; the funnel is adapted for injection of e-liquid for atomization;
      the multilayer nonwoven fabric is sheathed on the heating wire; the heating wire is disposed in the fixed seat; the insulation ring and the joint are sequentially disposed in the fixed seat in that order; the silicone gasket is sheathed on the fixed seat; the monolayer nonwoven fabric is sheathed on the fixed seat; the fixed seat is disposed in the limit cover; the first silicone seal is disposed on the limit cover;
      positive and negative terminals of the battery core are connected to the support assembly; the control plate is disposed on the support assembly; the third silicone seal is disposed on the support assembly; the support assembly is disposed in the support; the position limiter is disposed on the support; the third seal ring is sheathed on the support; the second magnet is disposed in the support; and
      the press button is disposed on the second housing; the support is disposed in the housing; and the decorative plate is attached to the housing.

* * * * *